United States Patent [19]

Grayzel

[11] Patent Number: 4,878,495

[45] Date of Patent: Nov. 7, 1989

[54] VALVULOPLASTY DEVICE WITH SATELLITE EXPANSION MEANS

[76] Inventor: Joseph Grayzel, 262 Fountain Rd., Englewood, N.J. 07631

[21] Appl. No.: 50,741

[22] Filed: May 15, 1987

[51] Int. Cl.$^4$ ............................................ A61M 25/00
[52] U.S. Cl. ................................ 128/344; 128/348.1; 604/101
[58] Field of Search ...................... 128/10, 344, 348.1; 604/96–103

[56] References Cited

U.S. PATENT DOCUMENTS

| | | | |
|---|---|---|---|
| 1,115,224 | 10/1914 | McAllum | 128/344 X |
| 2,854,982 | 10/1958 | Pagano | 604/101 |
| 3,046,988 | 7/1962 | Moreau et al. | 128/344 |
| 4,141,364 | 2/1979 | Schultze . | |
| 4,406,656 | 9/1983 | Hattler et al. . | |
| 4,456,011 | 6/1984 | Warnecke | 604/101 |
| 4,484,579 | 11/1984 | Meno et al. | 604/101 |
| 4,531,943 | 7/1985 | van Tassel et al. . | |
| 4,601,713 | 7/1986 | Fuqua . | |
| 4,655,746 | 4/1987 | Daniels jet al. | 128/348.1 |
| 4,681,564 | 7/1987 | Landreneau | 604/96 |
| 4,744,366 | 5/1988 | Jang | 604/101 X |

FOREIGN PATENT DOCUMENTS 0654214 2/1986 Switzerland ........................ 604/101

OTHER PUBLICATIONS

Valvuloplasty results get optimistic review–medical world news; Dec. 22, 1986; p. 72.
New Triple-Lumen Balloon Catheter For Percutaneous (Pulmonary) Valvuloplasty; Van Den Berg et al.; Catheterization & Card Iovascular Diagnosis 12:352-356 (1986).
Percutaneous transluminal balloon pulmonary valvuloplasty for the Relief of Pulmonary Valve Stenosis with Special Reference to Double-Balloon Technique-Khan, Yousef and Mullins American Heart Journal vol. 112, No. 1, pp. 158-166, Jul. 1986.
Percutaneous Balloon Valvotomy in Tricuspid Stenosis Zaibag, Robeiro and Kasab British Heart Journal 1987; 57:51-3.
Transluminal Balloon Valvotomy; A New Approach to the Treatment of Pulmonary-Valve Stenosis Radtke, Keane, Fellows and Lock Practical Cardiology vol. 13, No. 4, pp. 102–103, 107-108 & 113, Apr. 1987.
Assessment of Left Ventricular and Aortic Valve Function after Aortic Balloon Valvuloplasty in Adult Patients with Critical Aortic Stenosis McKay et al.; Circulation vol. 75, No. 1, Jan. 1987, pp. 191-203.
Percutaneous Transluminal Balloon Valvuloplasty of Adult Aortic Stenosis: Report of 92 Cases Cribier et al.; JACC vol. 9, No. 2, Feb. 1987; pp. 381-386.
Balloon Dilation of Mitral Stenosis in Adult Patients: Postmortem and Percutaneous Mitral Valvuloplasty Studies McKay et al.; JACC vol. 9, No. 4, Apr. 1987, pp. 723-731.
Percutaneous Balloon Aortic Valvuloplasty for Aortic Stenosis in Elderly Patients at High Risk for Surgery Schneider et al.; Annals of Internal Medicine 1987; vol. 106; pp. 696-699.
Percutaneous Dilation of an abdominal Aortic Stenosis Kumpe; Radiology vol. 141; pp. 536-538; Nov. 1981.

Primary Examiner—Dalton L. Truluck
Attorney, Agent, or Firm—Weingram & Zall

[57] ABSTRACT

The present invention provides a valvuloplasty device having a plurality of expandable chambers for valvuloplasty such that the arrangements and disposition of the expandable chambers conforms to the anatomy of the valve to be treated, thereby increasing the likelihood that inflation of the balloons will restore the valve more closely to its original anatomy and function. The expandable chambers can be expanded in various combinations or sequences in order to provide improved results from the treatment. The present invention also provides a method of performing valvuloplasty in which a plurality of expandable chambers having a fixed geometric relationship to each other are positioned within the valve to be treated and the expandable chambers are expanded in combination and/or in sequence to provide improved anatomical structure and function of the valve treated by the method.

24 Claims, 3 Drawing Sheets

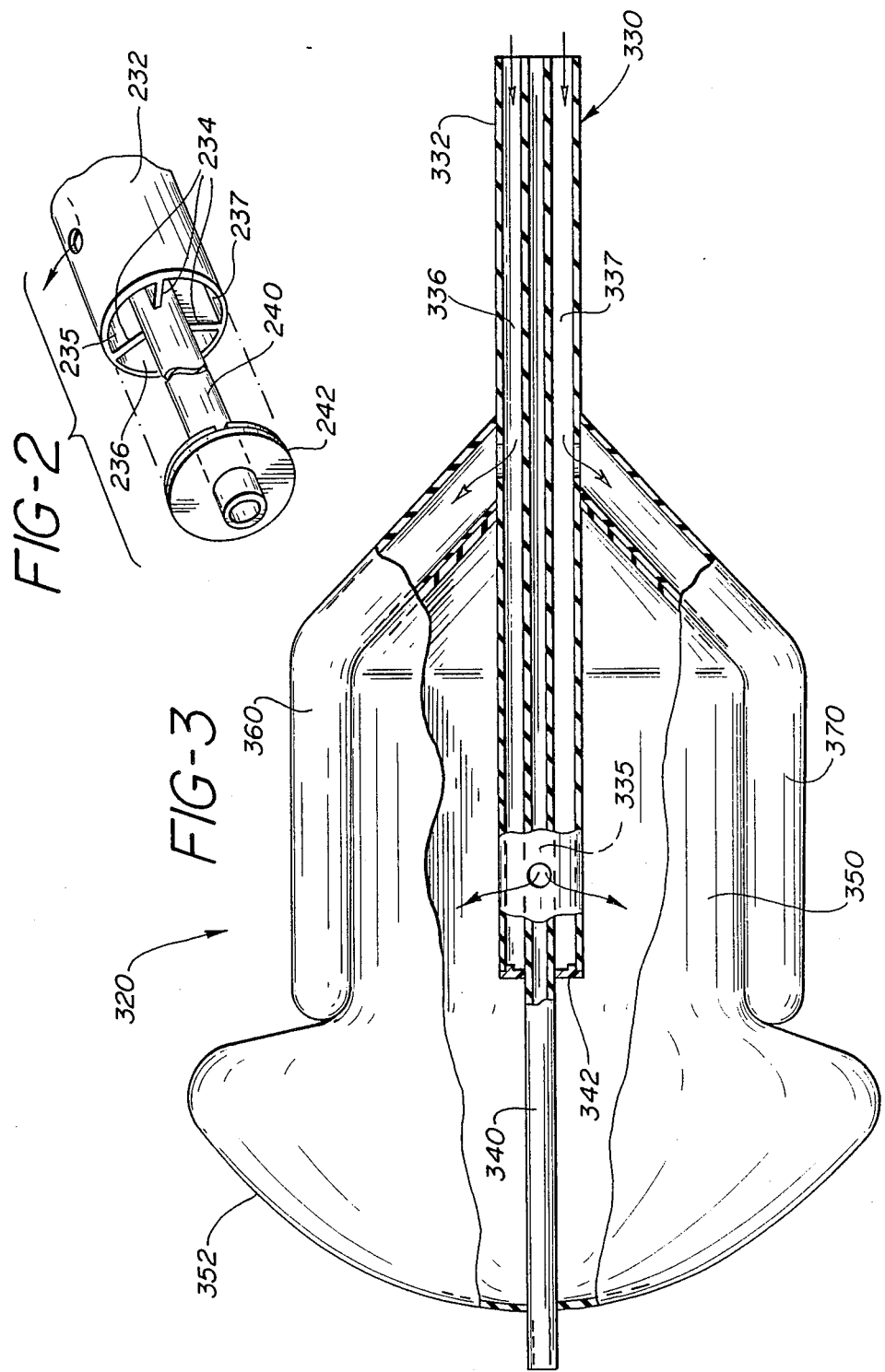

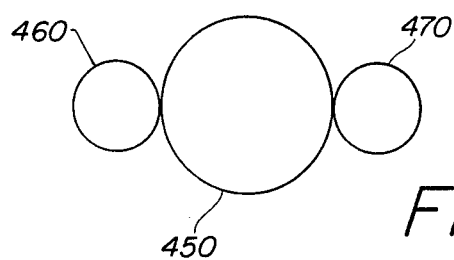
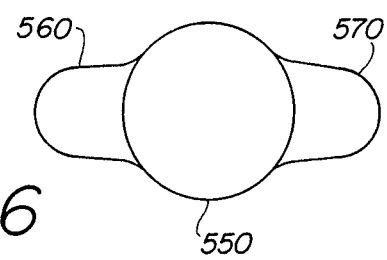
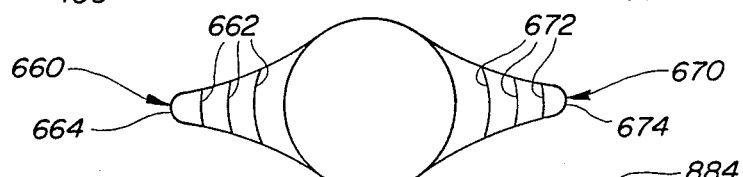
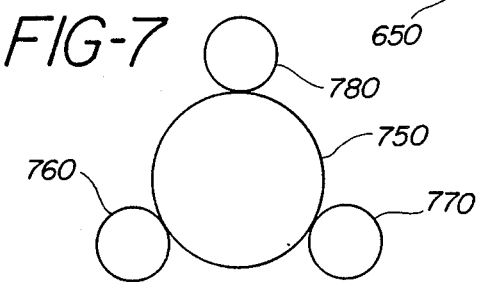
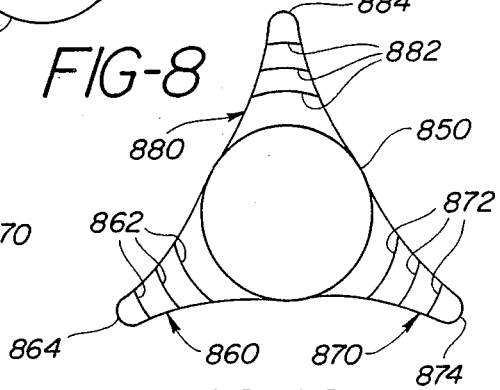
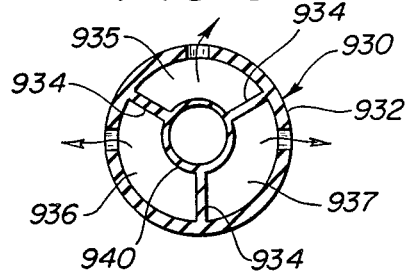
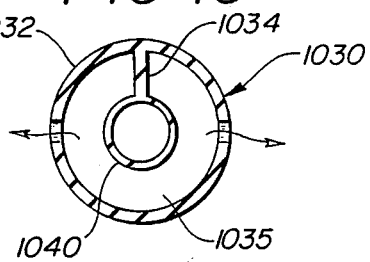
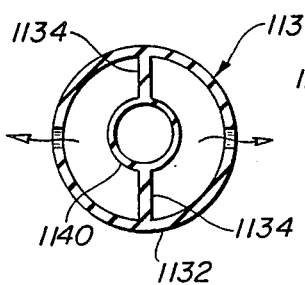
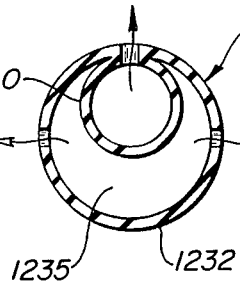
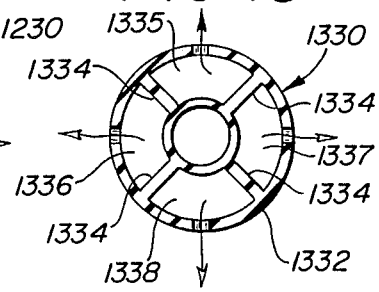

VALVULOPLASTY DEVICE WITH SATELLITE EXPANSION MEANS

BACKGROUND OF THE INVENTION

1. Field of the Invention

This invention relates to balloon valvuloplasty and, more particularly, to the method and apparatus for passing an expandable catheter into a valve of the heart and expanding the catheter to effect changes in the valve.

2. Description of the Prior Art

Stenosis, or narrowing of a valve's orifice, is a serious medical condition, generally the result of fusion and immobility of the valve leaflets. Stenosis may be congenital or may be acquired, as for example to sequel to rheumatic fever. In he past, traditional treatments of valvular stenosis have been surgical, employing open heart methods and techniques to either mobilize the existing valve leaflets or, more commonly, to insert a prosthetic valve of a mechanical nature or one derived from animal tissue.

These treatments are less than ideal. Surgery carries risk to life and large expense. Also, persons implanted with a mechanical valve must remain on anticoagulant medication for the remainder of their lifetime. Further, a significant disadvantage to insertion of mechanical valves in the heart is the problem or reliability of the mechanical device. Mechanical valves are subject to failure by fatigue or fracture of the constituent materials. The biologic valves (e.g. porcine or bovine material) are subject to degeneration of the tissues making up the valve.

Because of the shortcomings in the prior mechanical valves and the other difficulties inherent in the open heart methods developed, a relatively new technique of palliative nature has been developed, known as balloon valvuloplasty. In this procedure, a balloon mounted on a plastic tubular catheter is inserted into a blood vessel, passed into the heart and positioned with its deflated balloon member lying within the stenotic valve that is to be treated. The balloon is then inflated quickly with radio-opaque fluid several atmospheres' pressure. Fluoroscopy visualizes the expanding balloon and enables a judgement regarding the degree with which the valve leaflets have been rendered more mobile.

Balloon valvuloplasty has largely been performed with catheters carrying a single, cylindrical balloon of circular cross-section. In a significant proportion of such valvuloplasties, particularly involving the mitral valve whose leaflets present a somewhat elliptical or "fish-mouth" orifice, successful valvuloplasty has required the passage of two such balloon catheters across the mitral orifice side by side, and simultaneous inflation of both balloons. This requirement is made necessary because of the shape of the orifice ideally desired after treatment. Specifically, the mitral valve has only two leaflets and it is therefore necessary to be able to mobilize or "crack" the valve up to the portions of the valve commissures at the periphery of the valve ring, rather than only in the center of the valve.

Needless to say, simultaneous inflation of separate balloon catheters is a reatively difficult procedure requiring coordination of two separate catheters and is therefore more time consuming and riskier because of the difficulty in the simultaneous positioning of the catheters without mutual interference.

Attempts have been made to avoid the difficulties produced in the side-by-side or simultaneous operation of valvuloplasty balloons. An example of this is a "trifoil balloon having three balloons of equal size and shape. The balloons are disposed around the central catheter tube at intervals of 120°. The three balloons are commonly connected to the catheter lumen such that all three balloons inflate simultaneously. While suited for stenotic aortic pulmonic valves which are composed of three mobile semi-lunar leaflets, the "trifoil" balloon arrangement is not suitable for the mitral valve or for a congenitally bicuspid aortic valve. Even for use with stenotic aortic or pulmonic valves, the "trifoil" balloon cannot enter the narrower confines of the valve commissures without significant distortion of the balloon, which is unlikely.

Many patents have issued dealing with different types of expandable catheters. Examples of such patents are those to:

| | |
|---|---|
| Schultz | 4,141,364 |
| Hattler et al. | 4,406,656 |
| Van Tassel et al. | 4,531,943 |
| Fugua | 4,601,713 |

These patents, however, do not resolve the problems presently discussed.

Schultz, 4,141,364, discloses an expandable endotracheal or urethral tube which contains a number of sections which can be inflated. However, this device is not suited for, nor is it designed to deal with the problems of the specific shaped involved with the valvuloplasty procedure.

Hattler et al., 4,406,656, discloses multi-lumen catheters where fluid flowing in certain lumens causes these lumens to expand, and the absence of fluid-flow in the lumens causes the lumens to contract. As discussed at length in columns 1 and 2 of this patent, a number of prior-art patents relating to multi-lumen catheters are available. However, this patent does not deal with expandable catheters adapted for use in the valvuloplasty field.

Van Tassel et al., 4,531,943, teaches the use of a soft deformable member attached to the distal tip of a catheter. The deformable tip may comprise an inflatable balloon element attached to the distal end of the tip of the catheter. By selectively inflating the balloon tip, the effective area of the tip can be increased to reduce the overall force per unit area at a point of contract between the tip of the catheter and the blood vessel. However, this patent does not deal with the problem of the specialized shapes necessary for valvuloplasty.

Fugua, 4,601,713, deals with catheters applied to urology. the patent indicates that the so-called "Foley" catheter includes a tube with an inflatable cup or balloon at the distal end of the catheter so as to hold the catheter in place. Specifically, the balloon is inflated to retain the catheter in the bladder. However, the patent does not at all deal with catheters that would be suitable for use in valvuloplasty.

SUMMARY AND OBJECTS OF THE INVENTION

The present invention provides a valvuloplasty device having a plurality of balloons for valvuloplasty such that the arrangements and disposition of the balloons conforms to the anatomy of the valve to be treated, thereby increasing the likelihood that expansion of the balloons will restore the valve more closely to its original anatomy and function. The balloons can be inflated in various combinations or sequences in order to provide improved results from the treatment.

The present invention also provides a method of performing valvuloplasty in which a plurality of balloons having a fixed geometric relationship to each other are positioned within the valve to be treated and the balloons are expanded in combination and/or in sequence to provide improved anatomical structure and function of the valve treated by the method.

Accordingly, it is an object of the present invention to provide a valvuloplasty device having a plurality of balloons which can be inflated to more closely conform to the desired shape to be obtained in a valvuloplasty procedure.

Still another object of the present invention is to provide a valvuloplasty device having a plurality of balloons which enables the balloons to be inflated independently of each other during a valvuloplasty procedure.

Another object of the present invention is to provide a valvuloplasty device having a plurality of balloons in which the ballons can be independently expanded from separate pressure sources.

Yet another object of the present invention is to provide a valvuloplasty device having a plurality of balloons in which the end of the balloons can cover the end of the device.

A still further object of the present invention is to provide a valvuloplasty device having a plurality of balloons in which the device can extend beyond the end of the balloons to allow the device to be positioned along a predisposed spring guide.

Another object of the present invention is to provide a valvuloplasty device having a plurality of balloons in which the device includes a central large balloon and a plurality of satellite balloons to enable the device, when all balloons are expanded, to more closely resemble the shape that is desired for the particular valvular anatomy of the valve being treated by the valvuloplasty procedure.

Yet another object of the present invention is to provide a valvuloplasty device having a plurality of balloons in which the catheter is capable of exerting a greater force on the immobile leaflets of a stenotic valve and to direct such forces as to favor division of fused leaflets along the original commissural lines of separation.

A still further object of the present invention is to provide a valvuloplasty device having a plurality of balloons which balloon elements can be selectively directed at the valve commissures, into the remnant region of such commissures, and direct a specific force at the commissural line until disecting into the periphery of the valve ring.

Another object of the present invention is to provide a valvuloplasty device having a plurality of balloons which provides a centrally located balloon that inflates to enlarge the valvular orifice centrally while driving a plurality of satellite balloons in an outward direction.

A further object of the present invention is to provide a valvuloplasty device having a plurality of balloons which possesses a relatively large outer perimeter made up from a plurality of smaller individual balloons to enable higher inflation pressures for relatively thin wall-thicknesses of the balloon.

Yet another object of the present invention is to provide a valvuloplasty device having a plurality of balloons which includes a bulbous end at the end of a balloon to prevent expulsion of the balloon from the valve orifice by the cyclical blood pressures within the beating heart.

Still another object of the present invention is to provide a valvuloplasty devices having a plurality of balloons which can be used on bicuspid and tricuspid heart valves.

A further object of the present invention is to provide a valvuloplasty device having a plurality of balloons which can provide improved control and effectiveness in balloon valvuloplasty.

Another object of the present invention is to provide a valvuloplasty device having a plurality of balloons which includes a separate channel for a guide member to enable use with the Seldinger percutaneous technique or other like techniques.

It is yet another object of the present invention to provide a method of valvuloplasty employing a valvuloplasty device having a plurality of balloons in which method the balloons can be inflated separately to achieve different anatomical shape as desired during the valvuloplasty procedure.

Another object of the present invention is to provide a method of valvuloplasty employing a valvuloplasty device having a large central balloon and satellite balloons to enable separate dilation of the commissural regions and the central valvular orifice.

A still further object of the present invention is to provide a method of valvuloplasty including a multiple balloon valvuloplasty device which can be used in accordance with the Seldinger technique for insertion and guidance through the vascular channel.

Other objects and advantages will be apparent from the following description of the invention, the novel features being particularly pointed out hereinafter in the claims.

BRIEF DESCRIPTION OF THE DRAWINGS

FIG. 2 is a partial perspective view of the end portion of the central core of the device shown in FIG. 3;

FIG. 3 is a side view, partially in section, of a device similar to the device shown in FIG. 1, in the inflated state;

FIGS. 4–8 are schematic view of the cross-section of various balloons for valvuloplasty device built in accordance with the teachings of the present invention; and FIGS. 9–13 are various cross-sections of catheters for valvuloplasty device built in accordance with the teachings of the present invention.

DETAILED DESCRIPTION OF THE INVENTION

Figure 1:
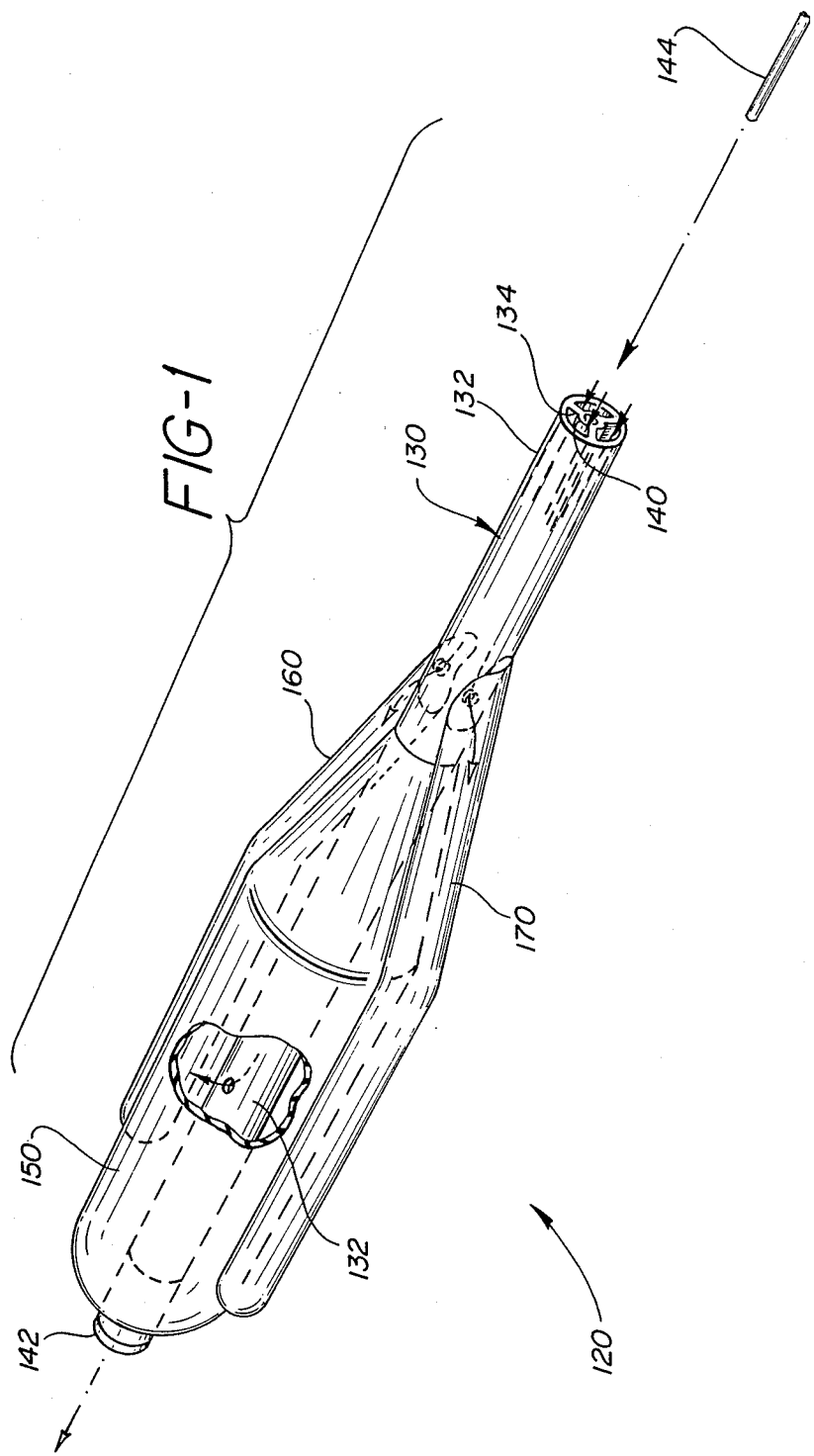
FIG. 1 is a perspective view, partially broken away, of a valvuloplasty device in the inflated state built in accordance with the teachings of the present invention.

As shown in FIG. 1, a valvuloplasty device generally indicated at 120 has a catheter portion 130 with an inner tubular core 140. A plurality of balloons consisting of a central balloon 150 and two sattelite balloons 160 and 170 which are fastened to the catheter portion.

FIGS. 2 and 3 show a modified embodiment of the invention, though similar with respect to many features. These similarities and distinctions will be apparent from the following discussion. In discussing the various figures, elements common to more than one figure may be referred to by the last two digits of the member.

As seen in FIGS. 1, 2, 3 and 9, the central member of the valvuloplasty device has a cylindrical tubular cross-section with an outer skin or wall 32 and a plurality of dividers 34, which dividers 34 divide the tubular section into three separate passages 35, 36 and 37. A hole or aperture in the top of passage 35 communicates the passage with the large central balloon 50 while other holes or apertures in passages 36 and 37 communicate the passage with the left and right satellite balloons 60 and 70, respectively. The passages 35, 36 and 37 can be connected to separate or single souces of pressurized liquid, such as isotonic saline, by any of the convenient conventional means presently known, to expnd the balloons. Additionally, various non-toxic radio-opaque dyes can be mixed with the pressurizing liquid to expand the balloons so that the position of the catheter can be easily seen by means of fluoroscopy during the valvuloplasty procedure.

The inner tubular core 40 of the catheter extends the length of the catheter and, as seen in FIGS. 2 and 3, extends beyond the end of the outer circumferentially disposed passages 35, 36, 37. A closure plate 42 seals the end of the circumferential fluid passages. The tubular extending core 40 allows for mounting or placing of the catheter core a guide wire which has previously been positioned within the vessel prior to introduction of the catheter.

As shown in FIG. 3, the end of the large central balloon is enlarged so that when the balloon is expanded, by introduction of a pressure fluid, the enlarged end of the balloon 352 expands beyond the dimensions of the adjoining satellite balloons 360 and 370 to act as a means for securing the position of the valvuloplasty device with respect to the valve that is being treated. The variation of pressures in the heart would tend to force the catheter back out of the valve. By having an end which is larger than the dimension of the valve being treated, it is assured that the catheter will be properly positioned during the valvuloplasty procedure and will not move.

It should be noted that the bulbous end of the valvuloplasty device is always to be positioned in the higher pressure side of the valve. In that position, surface 35 of the bulbous end will abut the ring of the valve to hold the valvuloplasty device in position.

As can be noted from examination of FIG. 1, the catheter portion of the valvuloplasty device 30 extends beyond the end of the central balloon. The entire end could be caped off, or the central core member 40 may remain open to allow for a guide wire, generally indicated at 44, to extend beyond the front of the catheter. Alternatively, as shown in FIG. 3, the fluid passages can be terminated within or before the end of the balloon portion of the valvuloplasty device with the catheter portion extending beyond the end of the balloon. Needless to say, it is also possible for the entire catheter portion including the core section 40 to terminate before the end of the balloon section.

In operation, the valvuloplasty device is directed into the orifice of the valve to be treated either by means of a pre-positioned guide wire or without such a guide. Such positioning is usually done with the aid of fluoroscopy.

Once the valvuloplasty device is in place, the valvuloplasty procedure can be undertaken with relative ease. Because there is a main balloon and one or more satellite balloons, which can be independently connected to the fluid passages in the catheter portion, a variety of shapes can be produced by selective expansion of the separate balloons.

As shown in FIGS. 4, 5 and 6, it is possible to produce valvuloplasty device of many configurations. FIG. 4 schematically shows a central balloon 450 having satellite ballons 460 and 470 which can be separate balloons fastened to the central balloon 450 or the outer wall of the catheter portion by any convenient fastening means. The central balloon 450 can be left unexpanded while the satellite balloons 460 and 470 can be first expanded to provide a relatively broad cross-section to allow for alignment and positioning of the catheter in bicuspid or "fish mouth" type valves. The central balloon 450 can then be explained which would tend to drive the satellites into the commissures of the valve to produce the heightened effect at the edges of the valve and thereby provide greater effectiveness of the valvuloplasty proceeding.

As shown in FIG. 5, another cross-section for a twin-satellite balloon valvuloplasty device has a central balloon 550 with sattelites 560 and 570. This configuration, however, would have a one-piece or continuous outer skin and therefore present a smoother, more continuous contacting surface during the valvuloplasty proceeding.

The configuration shown in FIG. 6 again has a large central balloon 650 with satellite balloons generally indicated at 660 and 670. However the satellite balloons include a plurality of ribs or partitions 662 and 672 respectively which partitions serve primarily for purposes of shaping the satellite balloons so that the balloons can have an oblong shape with relatively narrow edges 674 and 664 respectively. Such a shape facilitates access to the narrowest region of the valve for which the valvuloplasty proceeding is occurring. The balloons 660 and 670 could be independently inflated, if desired. Additionally, the partition sections 662 and 672 could be constructed to separate the satellite balloons into distinct segments, or sections, to enable the distinct sections of the satellite balloon to be separately expanded.

FIG. 9 was described somewhat in the discussions of FIGS. 1-3. FIGS. 9-13 are cross-sectional views of various central tubular catheter portions of the valvuloplasty devices. The views are schematic in nature in that the pathways from all passages are shown in FIGS. 9-13 in the same plane although they may not actually be so aligned. In FIG. 9, the central portin 930 has an outer cylindrical wall 932 which is divided by dividers 934 into three passages 935, 936 and 937. Each of the passages has one or more holes or apertures which communicate with the adjacent balloon to allow for the passage of the expanding liquid for that balloon.

As mentioned previously, the central core 940 provides a tubular section through which a guide could be inserted, or it could be used as another passage for pressure liquid.

FIG. 10 shows another variation of the catheter portion 1030 having an outer cylindrical section 1032 and an inner cross section 1040. A single divider 1034 positions the central core member from the outer wall 1032. Two apertures are positioned on opposite sides of the outer peripheral chamber 1035 and could be connected to two balloons to simultaneously expand the balloons. Of course, an additional aperture can also be formed so that three balloons can be inflated simultaneously. The inner chamber core 1040 can be used as a guide passage or could be used to expand a central balloon, depending on whether or not the catheter portion 1030 had a configuration similar to that shown in FIG. 3 with the core portion extending beyond the outer portions of the catheter portion.

FIG. 11 is similar to that of FIG. 10 with the addition of a second divider 1134 to divide the outer fluid carrying section into two distinct sections. The central core member 1140 can serve the same purpose as mentioned for the embodiment shown in FIGS. 9 and 10.

The embodiment of the central section shown in FIG. 12 is again similar in function to those of the outer embodiments shown in FIGS. 9–13, particularly FIG. 10 in that it only has two channels. The catheter portion 1230 has an outer cylindrical wall 1232 and in inner core section 1240. There are no dividers but there is only a single outer fluid passage 1235 with apertures on opposite sides to connect with the satellite balloons. The central core portion 1240 can have separate apertures for connecting to a central balloon. Alternatively, an additional set of apertures can be provided from flowpath 1234 to a central balloon, and core 1240 can be used for guide purposes.

FIG. 13 shows another embodiment of the catheter portion generally indicated at 1330 having an outer wall 1332 and a plurality of dividers 1334 which separate the section into an upper passage 1335, left and right side passages 1336 and 1337, and bottom passage 1338. The central core portion 1340 serves the function, in this case, of acting as a guide only since there are four separate flow passages which would be sufficient to separately inflate a central balloon member and three satellite balloons.

Referring to FIGS. 7 and 8, we see a schematic representation of the cross-section of a three-satellite balloon embodiment of the invention. FIG. 7 is substantially similar to FIG. 4 in that is has a central balloon 750 and satellites having circular cross-sections. The satellites consist of lower left and lower right satellite balloons 760 and 770 and a top, or dorsal, balloon 780 is also present. The three baloons can operate in much the same manner as the two balloon configuration previously shown. These three balloon embodiments are, of course, adapted for use with valvuloplasty procedures for tricuspid valves.

FIG. 8 is a tri-satellite ballon configuration similar to FIG. 6 in that the satellite portions are partitioned. A central balloon 850 has three satellite balloons; a top satellite 880, a lower left and lower right satellite balloon 860 and 870 respectively. Each segment has a plurality of separator or partition members 862, 872 and 882 respectively, which members are primarily for the shaping of the satellites to enable a desirable tapered shape having relatively narrow ends 864, 874 and 884, respectively, which will allow for positioning of the balloons into the narrowest portion of the valve. As with the embodiment shown in FIG. 6, the partition members 862, 872 and 882 could also be used to separate the satellite balloons into separate sections which could be separately expanded.

The method of performing the valvuloplasty procedure using the apparatus described is straightforward. The first step is to position the valvuloplasty device within the valve to be treated. The positioning can be done either with or without the aid of a guide wire which has first been inserted through the area to be treated.

Once the valvuloplasty device is in place, any combination or sequence of expansion can be produced with the plurality of balloons that comprise the embodiment of the invention. The central balloon can be expanded at a relatively low pressure so that the enlarged end of the balloon will expand sufficiently greater than the area of the valve being treated to ensure that the catheter will be securely positioned. The sattelite balloons can then be partially inflated to provide a non-circular or irregular profile or cross-section that will facilitate proper positioning of the balloons within the irregular orifice of the valve to be treated to obtain a maximum beneficial effects from the valvuloplasty procedure. The satellite balloons can then be expanded to maximum pressure to produce the desired cross-sectional configuration and forces to drive the satellite into the commissures of the valve. After expansion of the satellites, the central balloon can be expanded to further drive the edges of the satellite balloons into the commissures of the valve.

The balloons are not intended to remain expanded for a significant period of time since, when expanded, they tend to occlude the blood flow through the valve and disrupt the functioning of the heart. Therefore,, it is envisioned that the expansion of the balloons will be of relatively short duration and/or a series of pulses sequenced in some way with the beating of the heart.

In certain circumstances, it may be desirable to first expand the central balloon of the catheter rather than one satellite balloons to thereby determine if sufficient function can be obtained from the valve by merely treating the central portion of the valve as distinguished from the edge portions.

Additionally, it may be beneficial to sequence the expansion of the central balloon before the expansion of the satellite balloons in order to partially spread the commissures thereby facilitating entry of the satellites to the commissures.

From the above detailed description of the invention, it should be noted that the present invention provides a more effective method of valvuloplasty in which it is possible for the valvuloplasty device to conform to the detailed anatomy of the valve to be treated. The previous valvuloplasty devices are relatively unsuitable for access to the commissures of the valve so that treatment occurred primarily in the central area of the valve. By being able to work at the peripheral edges of the valves, far superior valvuloplasty results should be obtainable. Additionally, the use of the guide in collaboration with a bulbous end on the central balloon stabilizes the position of the valvuloplasty device during the course of the procedure thereby enhancing the accuracy of the valvuloplasty procedure. Not only is the axial positioning of the valvuloplasty device enhanced by means of a guide wire and an enlarged bulbous end, but, in addition, the ability to separately expand satellite balloons will ensure enhanced radial positioning of the valvuloplasty device for the valvuloplasty procedure.

It should be pointed out that, while the embodiments shown have a cylindrical catheter portion, the catheter portion need not be cylindrical but could be composed of separate tubes of cylinders joined together in a variety of patterns, either as a ribbon of passageways or by various other means.

While several embodiments of the invention have been illustrated and described, it is apparent that many other variations may be made in the particular design and configuration without departing from the scope of the invention as set forth in the appended claims.

I claim:

1. A balloon catheter for valvuloplasty comprising:
a catheter portion having a plurality of flow passages therein;
primary expandable means coupled to a source of pressurized liquid;
auxiliary expandable means coupled to a source of pressurized liquid;
said auxiliary expandable means mounted circumferentially adjacent said primary expandable means with the axis of said primary and auxiliary expandable being displaced and capable of being expanded under control of said liquid supply separately and independently of the expansion of said primary expandable means and in substantially parallel relation to the primary expandable means said auxiliary expandable means being displaced laterally from the axis of said primary expandable means upon expansion of said primary expandable means.

2. The device of claim 1 wherein each of said expandable means communicates with separate fluid paths in said catheter portion of said catheter.

3. The device of claim 1 wherein said auxiliary expandable means consisting of at least one separately expandable chamber.

4. The device of claim 1 wherein said auxiliary expandable means consisting of two separately expandable chambers.

5. The device of claim 1 wherein said auxiliary expandable means consisting of three separately expandable chambers.

6. The device of claim 1 wherein said first expandable means further comprises a large expansible end portion adapted to expand to an area greater than the area of the remaining portion of the first expandable means to act as a retaining means for the device when properly positioned for valvuloplasty.

7. The device of claim 1 wherein said auxiliary expandable means comprise partition means within said expandable means to shape said auxiliary expandable means when in the expanded state.

8. The device of claim 7 wherein said partition means shape said auxiliary expandable means to produce a relatively narrow rounded edge of said auxiliary exandable means.

9. The device of claim 7 wherein said partition means separate said auxiliary expandable means into separate and distinct compartments which can be independently expanded.

10. The device of claim 1 further comprising guide means extending through one of said expandable means to enable said device to be moved along said guide means to position said device.

11. The device of claim 10 wherein said guide means extend through said first expandable means.

12. A balloon catheter valvuloplasty device comprising:
a central catheter portion;
a plurality of liquid glow paths in said central section;
a guide passage in said central catheter portion;
first expandable means connected to said central catheter portion and communicating with one of said liquid flow paths to expand upon introduction of pressurized liquid therein;
auxiliary expandable means comprising a plurality of separately expandable chambers mounted circumferentially adjacent to and in substantially parallel relation to the primary expandable means;
each of said separately expandable chambers communicating with a separate fluid path in said central section;
said first expandable means including an enlarged end section adapted to expand larger than the area of a valve to be treated to position and anchor the device during a valvuloplasty proceeding;
at least one of said separately expandable chambers comprising a plurality of partition means;
said partition means shaping said separately expandable chamber to produce a relatively narrow rounded edge thereof; and
guide means extending through said central means and through said first expandable means for housing a guide wire for positioning of said catheter.

13. A balloon catheter valvuloplasty device comprising:
a primary expandable chamber;
at least one satellite expandable chamber circumferentially adjacent and in substantially parallel relation to the primary expandable means with the axis of said primry and auxiliary expandable means being displaced;
a central catheter portion having flow passage means therein;
said flow passage means communication with a source of pressurized fluid for expanding said primary and satellite expandable chambers;
said primary and satellite expandable chambers communicating with said flow passage means;
said primary and satellite expandable means in fixed position with relation to each other; and
said auxiliary expandable means being displaced laterally from the axis of said primary expandable means upon expansion of said primary expandable means.

14. The device of claim 13 wherein said flow passage means communicating with a source of pressurized fluid for expanding said primary and satellite expandable chambers consisting of a single flow passage communicating with the primary and satellite expandable chamber means.

15. The device of claim 1, 12 or 13 wherein said first expandable means is centrally located.

16. A method of performing valvuloplasty on a valve associated with the heart comprising the steps of:
placing a valvuloplasty device adjacent a valve to be treated by valvuloplasty said valvuloplasty device having a primary expandable chamber and at least one auxiliary expandable chamber mounted circumferentially adjacent to said primary expandable chamber and adapted to expand parallel to the primary expandable chamber;
a positoning the valvuloplasty device across the plane of the valve;
expanding expandable chamber and at least one auxiliary expandable chamber associated with said valvuloplasty device of flex or open the segments of the valve to be treated;
contracting the expandable chambers; and
removing the valvuloplasty device from the valve.

17. The method of valvuloplasty according to the method of claim 16 wherein the step of placing a valvuloplasty device adjacent a valve to be treated by valvuloplasty includes the stept of guiding the valvuloplasty device along a guide passing through the valve to be treated.

18. The method of valvuloplasty according to the method of claim 16 wherein said valvuloplasty device includes an enlarged forward section and further comprising after the step of positoning the valvuloplasty device, the step of securing the valvuloplasty device by expanding the enlarged forward section of an expandable chamber associated with the valvuloplasty device beyond the valve.

19. The method of valvuloplasty according to the method of claim 16 wherein the step of positioning the valvuloplasty device includes the step of auxiliary positioning the valvuloplasty device by means of inflating an enlarged forward section of the main expansion balloon.

20. The method of valvuloplasty according to the method of claim 16 wherein the step of positioning the valvuloplasty device includes the step of rotationally positioning the valvuloplasty device by inflating an auxilary expandable chamber before inflating the primary expandable chamber.

21. The method of valvuloplasty according to the method of claim 16 wherein the step of expanding the main expandable chamber and at least one auxiliary expandable chamber includes the steps of sequentially expanding the auxiliary expandable chamber prior to expansion of the primary expansion chamber so that expansion of the primary chamber will drive the auxiliary expansion chamber into the commissures or narrow portions of the valve to be expanded.

22. The method valvuloplasty according to the method of claim 16 wherein the step of expanding the main expandable chamber and at least one auxiliary chamber includes the step of expanding auxiliary and primary expansion chambers together.

23. The method valvuloplasty according to the method of claim 16 wherein the step of expanding the main expandable chamber and at least one auxilariy chamber includes the step of expanding the primary expansion chamber before the auxiliary expansion chamber.

24. A method of performing valvuloplasty on a valve associated with the heart comprising the steps of:
  placing a valvuloplasty device adjacent a valve to be treated by valvuloplasty by guiding the valvuloplasty device along a guide passing through the valve to be treated said valvuloplasty device having a plurality expandable chamber and at least one auxiliary expandable chamber mounted circumferentially adjacent said primary expandable chamber and adapted to expand parallel to the primary expandable chamber;
  axially positioning the valvuloplasty device across the plane of the valve by means of inflating an enlarged forward section of the primary expansion chamber;
  rotationally positioning the valvuloplasty device within the plane of the valve by at least partially expanding an auxiliary expandable chamber before inflating the primary expandable chamber; and
  expanding the primary and auxiliary expandable chamber in sequence to flex or open the segments of the valve to be treated by sequentially expanding one of the auxiliary expandable chambers or the primary chamber prior to the other chamber to drive the auxiliary expandable chamber into the commissures or narrow portions of the valve to be expanded when both primary and auxiliary balloons are expanded.

* * * * *